United States Patent [19]

Kimura et al.

[11] Patent Number: 5,126,436

[45] Date of Patent: Jun. 30, 1992

[54] PHYSIOLOGICALLY ACTIVE SN-198C COMPOUNDS

[75] Inventors: Kenichi Kimura; Shoji Nakayama; Nobuo Miyata, all of Utsunomiya, Japan

[73] Assignee: Snow Brand Milk Products Company Limited, Hokkaido, Japan

[21] Appl. No.: 528,397

[22] Filed: May 25, 1990

[30] Foreign Application Priority Data

May 26, 1989 [JP] Japan .................................. 1-133036

[51] Int. Cl.$^5$ ............................................. C07H 17/00
[52] U.S. Cl. .................................... 536/17.4; 536/6.2; 536/16.8; 435/105; 435/253.54
[58] Field of Search ................ 435/105; 536/6.2, 17.4, 536/16.8

[56] References Cited

FOREIGN PATENT DOCUMENTS 50-132183  5/1974  Japan .
61-291594 12/1986  Japan .

OTHER PUBLICATIONS

The Journal of Antibiotics, vol. XL, No. 2, 1987, "New Piericidin Glucosides, Glucopiericidins A and B", pp. 149–156.

Primary Examiner—Johnnie R. Brown
Assistant Examiner—Pamela S. Webber
Attorney, Agent, or Firm—Millen, White & Zelano

[57] ABSTRACT

Physiologically active material SN-198C producing bacteria are disclosed which belong to Streptomyces species and products which have the following structural formula:

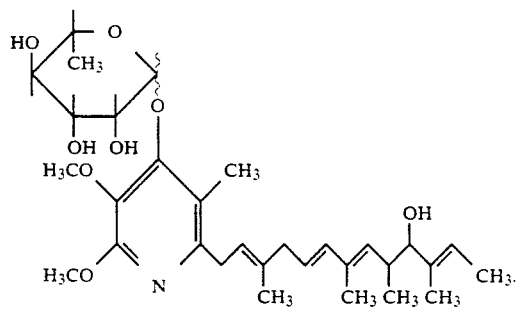

4 Claims, 4 Drawing Sheets

PHYSIOLOGICALLY ACTIVE SN-198C COMPOUNDS

BACKGROUND OF THE INVENTION

1. Field of the Invention

The present invention relates to novel physiologically active material SN-198C production bacteria, novel physiologically active material SN-198C's and a method for preparing the same. The material of the present invention is useful as an antibacterial agent or an anticancer.

2. Description of the Related Art

It is well known that microorganisms such as Actinomycetes produce various physiologically active materials. For example, Japanese Laid-open Patent Publication No. 50-132183 discloses that Streptomyces piericidics seino produces a series of compounds comprising piericidins A to P called piericidins. Furthermore, Japanese Laid-open Patent Publication No. 61-291594 discloses a novel compound SS48727E in which D-glucose is bonded to the hydroxyl group at the $C_3'$ position of piericidin A1. It has been confirmed that the piericidins have physiological activities such as antibacterial function, antitumor effect, insecticidal effect and antihypertensive function.

SUMMARY OF THE INVENTION

The present inventors have separated microorganisms from soil, cultured them, and investigated materials produced in its culture medium. As a result, they have found that a bacterial strain separated from the soil in Ishibashi-machi, Shimotsuga-gun, Tochigi, Japan produces SN-198C which is a novel kind of piericidins, and the present invention has been completed on the basis of this discovery.

Thus, a main object of the present invention is to provide a novel physiologically active material SN-198C which is a novel piericidin compound, and a method for preparing the new material.

DETAILED DESCRIPTION AND PREFERRED EMBODIMENT

Figure 1:
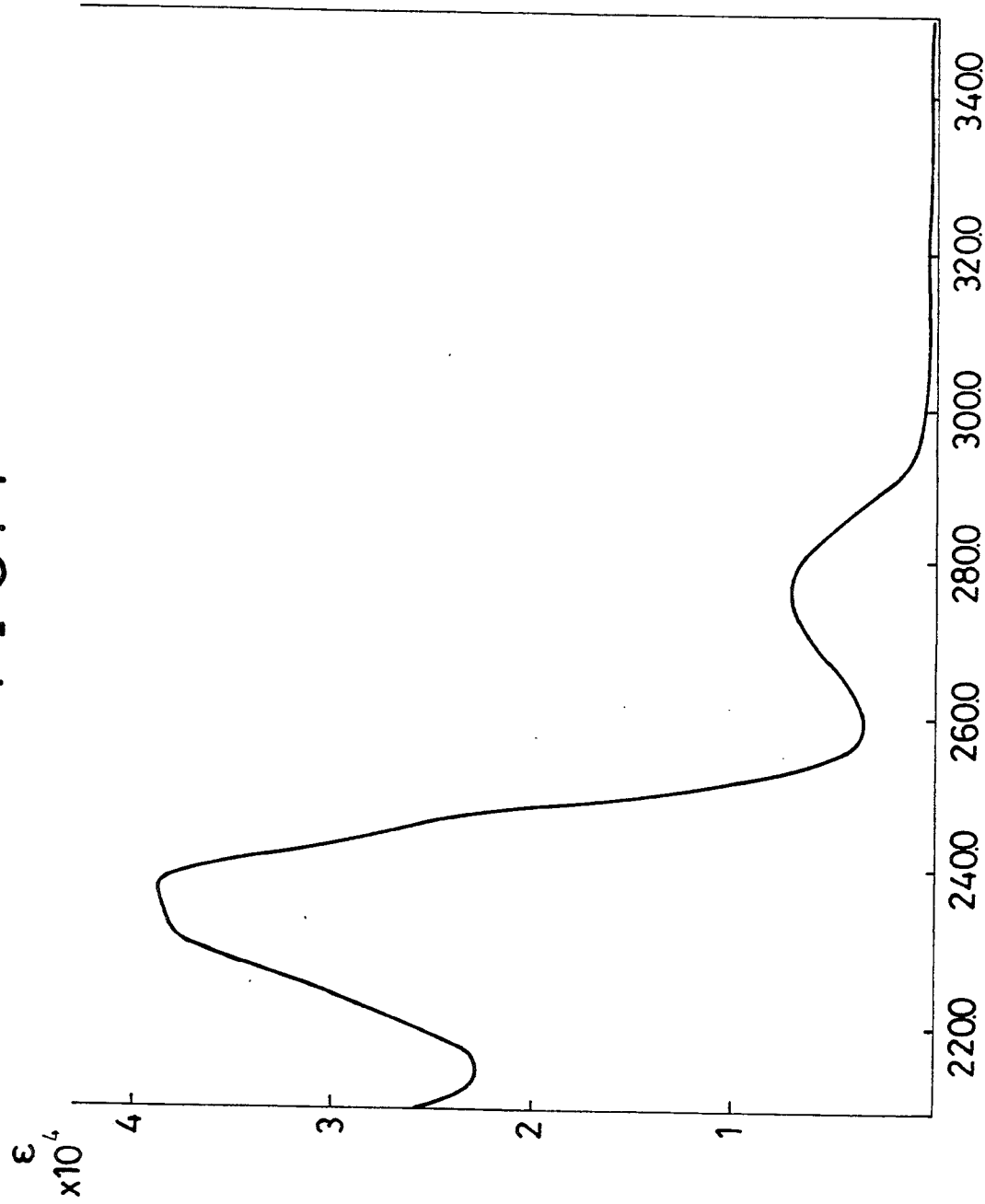
FIG. 1 shows an ultraviolet absorption spectrum of the SN-198C material.

A novel physiologically active material SN-198C of the present invention is a compound having the following structure in which rhamnose is bonded to the $C_3'$ position of a piericidin. Furthermore, it should be noted that the present invention covers a series of compounds in which the OH of the piericidin is replaced with $CH_3$ or $OCH_3$. In the present invention, such a series of compounds are called SN-198C's:

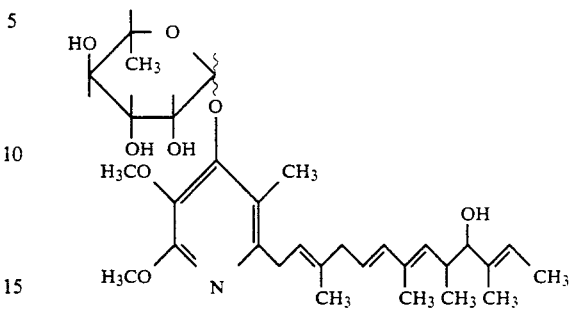

A bacterial strain which can produce the physiologically active material SN-198C of the present invention, i.e., the SN-198 strain, has the following bacterial characteristics:

(1) Morphological Properties

In a culture medium, submerged mycelia branch and well extend, and they are not cut under usual conditions. The aerial mycelia abundantly adhere to a yeast-/malt agar culture medium (ISP culture medium No. 2), and the formation of spores is good. Each branch of the aerial mycelia is a single branch, and any radial branches cannot be seen. The branches are not so much. Any sporangia, sclerotiums and flagellum spores are not observed. A long spore chain of arthrospores is formed at the tip of each mycelium, and each chain is composed of 20 or more of the arthrospores. According to observation by the use of a scanning type electron microscope, it can be confirmed that the mycelia and the spore chains mainly have a linear morphology, and at times, some of them have a twice or thrice finely spiraled morphology. Each spore has a short cylindrical shape, a diameter of 0.6 to 0.9× and a length of 0.7 to 1.7 microns, and the surface of the spore is smooth.

(2) Growth Condition on Various Culture Media

Cultivation is made at a temperature of 27° C. for a period of from 14 to 21 days on various culture media (9 kinds), and as a result, it is elucidated that the SN-198 strain can grow extremely well on a yeast extract/malt extract agar medium (ISP, No. 2), an oatmeal agar medium (ISP, No. 3) and an inorganic salt/starch agar medium (ISP, No. 4). On a peptone/yeast extract/iron agar medium (ISP, No. 6), a sucrose/nitrate agar medium, a glucose/asparagine agar medium and a nutrient agar medium, the growth of the SN-198 strain is moderate. However, on a glycerin/asparagine agar medium (ISP, No. 5) and a tyrosine agar medium (ISP, No. 7), the growth of the SN-198 strain is poor. The results of the observed growth condition are set forth in Table 1.

TABLE 1

| | Growth Condition on Various Culture Medium | | | | |
|---|---|---|---|---|---|
| Culture Medium | Growth | Color on Back Surface | Adhesion and Color of Hypha | | Soluble Dyestuff |
| Yeast Extract/Molt Extract Agar (ISP No. 2) | Good | Light Yellow [5Y 9/6] | Abundant | Gray [0 6/N] | None |
| Oatmeal Agar (ISP No. 3) | Good | Greenish White [5GY 9/2] | Abundant | Dark Brown [5R 2/1] | None |
| Inorganic Salt/Starch Agar (ISP No. 4) | Good | Yellow White [5Y 9/2] | Abundant | Dark Brown [5R 2/1] | None |
| Glycerin/Asparagine Agar | Poor | Ivory | Poor | Ivory | None |

TABLE 1-continued

| | Growth Condition on Various Culture Medium | | | |
|---|---|---|---|---|
| Culture Medium | Growth | Color on Back Surface | Adhesion and Color of Hypha | Soluble Dyestuff |
| (ISP No. 5) | | [10YR 6/3] | | [10/YR 6/3] | |
| Peptone/Yeast Extract/ Iron Agar (ISP No. 6) | Moderate | Light Ivory [10YR 7/3] | Moderate | Light Reddish Brown [5R 6/2] | None |
| Tyrosine Agar (ISP No. 7) | Poor | Ivory [10YR 6/3] | Poor | Ivory [10YR 6/3] | None |
| Sucrose/Nitrate Agar (Waksman No. 1) | Moderate | Yellowish Gray White [5Y 3/1] | Moderate | Gray [0 8/N] | None |
| Glucose/Asparagine Agar (Waksman No. 2) | Moderate | Yellowish White [5Y 9/2] | Moderate | Gray [0 8/N] | None |
| Nutrient Agar (Waksman No. 14) | Moderate | Light Ivory [10YR 8/3] | Moderate | Light Reddish Brown [5R 7/2] | None |

(3) Physiological Properties (a) Growth temperature: The SN-198 strain grew at a temperature of from 15° to 37° C. in a yeast extract/malt extract agar medium. However, the strain could not grow at 42° C., and after 10 days, this temperature was returned to 27° C., but at this time, the bacteria were dead.

(b) Liquefaction of gelatin: Impossible (c) Decomposition of starch: Possible (d) Conversion of skim milk into peptone: Impossible (growth in the skim milk was impossible) Coagulation of skim milk: Impossible (e) Production of melanine-like dye: Possible (f) Reduction of nitrate: Possible (4) Anabolism of Carbon Source For Pridham/Gottlieb media to which 1% of each of various carbon sources was added, anabolism was observed. The results are as follows:

| | |
|---|---|
| D-glucose | anabolized |
| D-xylose | anabolized |
| L-arabinose | anabolized |
| L-rhamnose | not anabolized |
| D-fructose | anabolized |
| D-galactose | anabolized |
| raffinose | not anabolized |
| D-mannitol | not anabolized |
| i-inositol | not anabolized |
| salicin | not anabolized |
| sucrose | anabolized |
| D-ribose | not anabolized |
| xylitol | not anabolized |
| dulcitol | not anabolized |
| D-mannose | anabolized but indefinite |
| lactose | not anabolized |
| D-cellobiose | anabolized |

(5) Composition of Cell Wall

In accordance with Lechevalier et al.'s process [Int. J. Syst. Bacteriol., 20, p. 435–443 (1970)], 2,6-diaminopimelic acid in mycelia of the SN-198 strain was analyzed, and in consequence, it was confirmed that 2,6-diaminopimelic acid was of an LL type (I type cell wall).

In view of the above-mentioned characteristics, it was judged that the bacteria of the SN-198 strain are microorganisms (Actinomycetes) which belong to Streptomyces species, and so they were named Streptomyces species SN-198.

For the determination of the species of the SN-198 strain, more careful investigation is necessary. Search was made in reference to Bergey's search book, "Determinative Bacteriology", and it was apparent that the properties of the SN-198 strain were closest to the content of the description regarding *Streptomyces cirratus*.

However, the *Streptomyces cirratus* does not produce the SN-198C material, whereas the SN-198 strain produces it, and thus both of them are different from each other in this point. Even when the SN-198 strain was subcultured, these properties did not change, and so it was judged that the SN-198 strain is a new variant of the *Streptomyces cirratus*.

The present inventors have deposited the SN-198 strain under trust No. FERM P-10480 in Agency of Industrial Science and Technology, Fermentation Research Institute with the intention of discriminating the SN-198 strain having the above-mentioned properties from other known strains.

Generally, with regard to the Actinomycetes, characteristics tend to change, and spontaneous mutation is liable to occur. Furthermore, the Actinomycetes can be easily mutated by an artificial mutation treatment such as irradiation of ultraviolet rays or cobalt 60, or a treatment using a chemical mutation induction agent. In the present invention, all of mutated SN-198 strains can also be utilized, so long as they have the ability to produce the SN-198C material.

Now, reference will be made to a process for first cultivating the above-mentioned SN-198C production strain and then obtaining the desired SN-198C material.

In cultivating the physiologically active material, SN-198C material production strain, which belongs to the Streptomyces species, a usual cultivation technique for the Actinomyces can be employed. A nutrient medium is used, and as this kind of medium, any of a natural medium, a synthetic medium and a semisynthetic medium can be used, so long as it contains a carbon source, a nitrogen source, minerals and trace nutrient components. As the carbon source, saccharides such as glucose, fructose, sucrose and galactose as well as starch can be used singly or in combination. Furthermore, a hydrocarbon, an alcohol or an organic acid such as citric acid is also usable as the carbon source, depending upon the assimilability of the bacteria. Examples of the nitrogen source include inorganic compounds such as ammonium chloride, ammonium nitrate and sodium nitrate, organic compounds such as urea and sodium glutamate, and soybean powder, dried yeast, peptone, meat extract, proteose peptone, Casamino acid, isopeptone and corn steep liquor, and they can be used singly or in combination. Examples of the minerals include calcium carbonate, sodium chloride, potassium chloride, phosphates, copper sulfate, manganese sulfate, zinc sulfate and iron sulfate, and they can be used singly or in combination in compliance with need. In addition, if necessary, the nutrient components can be added to the culture medium which are, for example, biotin, pantothenic acid, pyridoxine, niacin and inosine. For the purpose of erasing foam generated during the cultivation, a defoamer such as silicone oil can be added thereto.

A usual cultivation process can be employed, and shak culture or aeration spinner culture is most suitable. Culture temperature is from 20° to 35° C., preferably from about 25° to about 30° C. With regard to the physiologically active material SN-198C, the peak of the production is present at the point of time when a period of from 48 to 96 hours has passed since the start of the cultivation. Therefore, it is preferred that when the concentration of the product in the culture medium has reached a maximum level, the cultivation is stopped, and the desired product is then isolated and purified.

The recovery of the SN-198C material from the culture medium should be carried out taking physical and chemical properties of the product into consideration. Since the SN-198C material is present in the filtrate of the culture medium and in the bacteria themselves, the latter are separated from the culture medium by centrifugal separation or filtration, and the product is recovered and purified from the bacteria and the filtrate of the culture medium by one or a combination of solvent extraction, chromatography such as ion exchange chromatography, adsorption chromatography, partition chromatography or gel filtration, dialysis, precipitation and ultrafiltration.

An example of the usual recovery and purification process is as follows:

After completion of the cultivation, the bacteria are separated from the culture medium by centrifuging or filtration. The bacteria are then extracted with a suitable solvent such as acetone or methanol, and the resulting extract is then concentrated under reduced pressure. After the solvent has been removed therefrom, extraction is effected by the use of a solvent such as ethyl acetate. The culture medium is likewise extracted with the same solvent, and the thus obtained extract is then joined to the above extract. Afterward, the solvent is distilled off from the extract, and the residue is washed with n-hexane or petroleum ether and then subjected to silica gel column chromatography. Next, the product is eluted with a chloroform/methanol solution in order to recover the SN-198C fraction. The latter is further treated through a reversed phase HPLC, whereby the desired SN-198C material is purified.

The thus obtained SN-198C material has the following physical and chemical properties:

Physical and chemical properties (1) Elemental analysis

|  | C | H | N |
|---|---|---|---|
| Found (%) | 64.82 | 8.30 | 2.40 |
| Calcd. (%) | 65.26 | 8.42 | 2.46 |

(2) Molecular formula: $C_{31}H_{47}NO_8 \cdot \frac{1}{2}H_2O$ (3) Mass spectrum (FAB-MS): m/z 562 (M+H)+

(4) Specific rotation: $[\alpha]_D^{27} = -44.0°$ C. (C=0.1, methanol)

(5) Ultraviolet absorption spectrum: FIG. 1: $\lambda$MeOH-max nm ($\epsilon$): 232 (37000), 238 (37800), 277 (6700)

Figure 2:
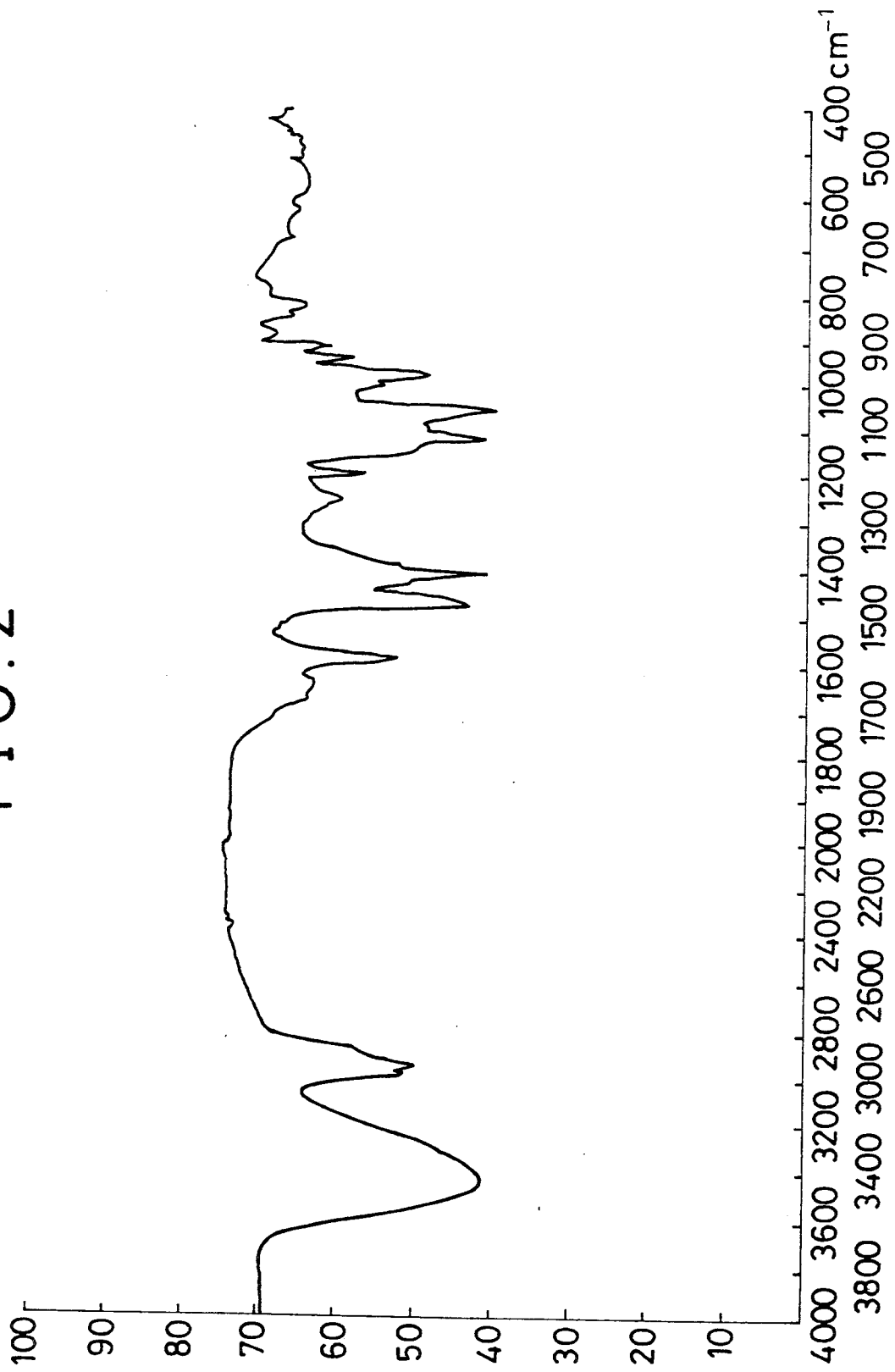
FIG. 2 shows an infrared absorption spectrum of the SN-198C material measured by a KBr method.

(6) Infrared absorption spectrum (KBr method): FIG. 2

Figure 3:
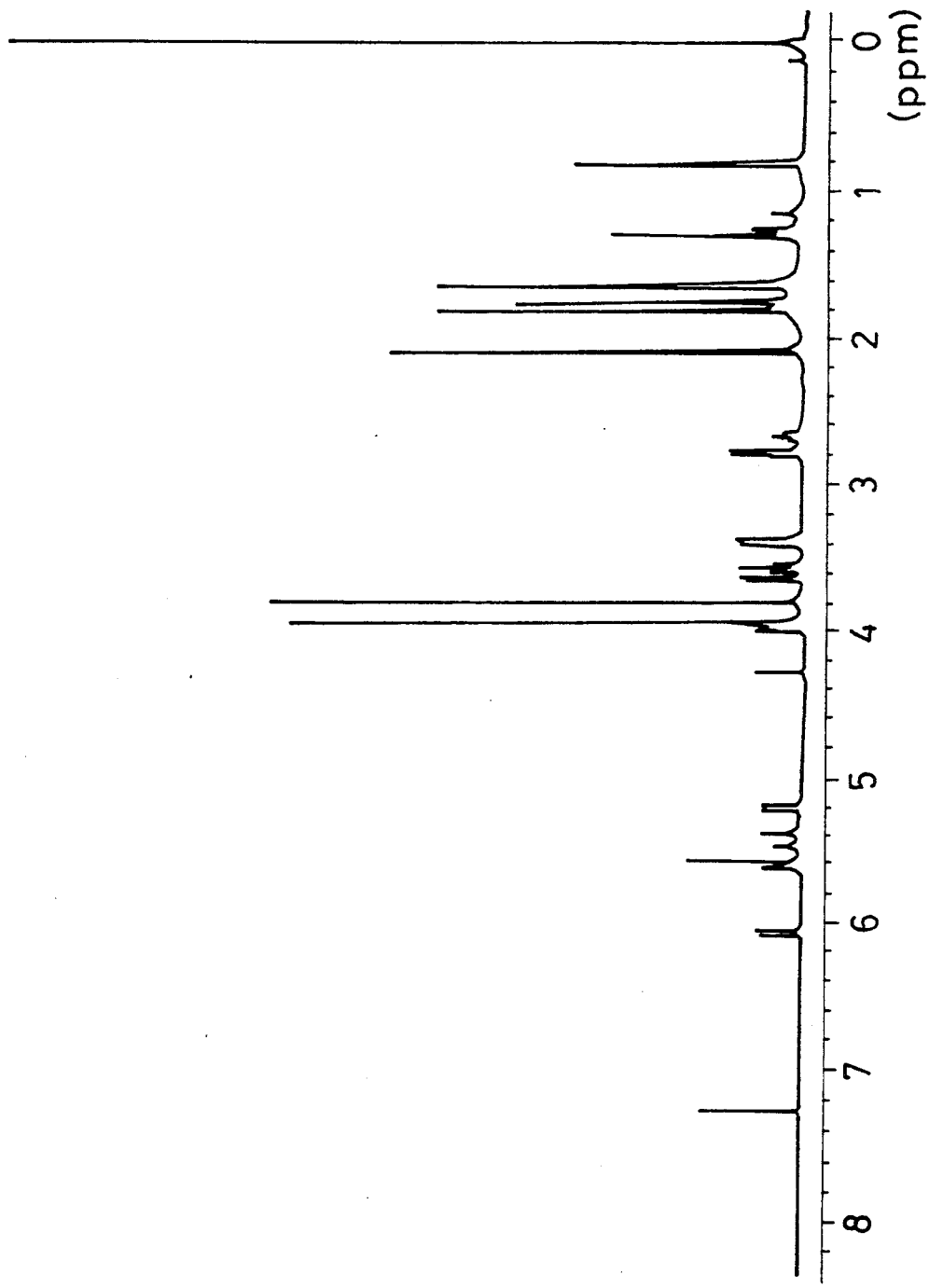
FIG. 3 shows $^1$H-NMR spectrum of the SN-198C material.

(7) $^1$H-NMR Spectrum (500 MHz): FIG. 3

Measurement was made in a deuterated chloroform solution on the basis of TMS.

Figure 4:
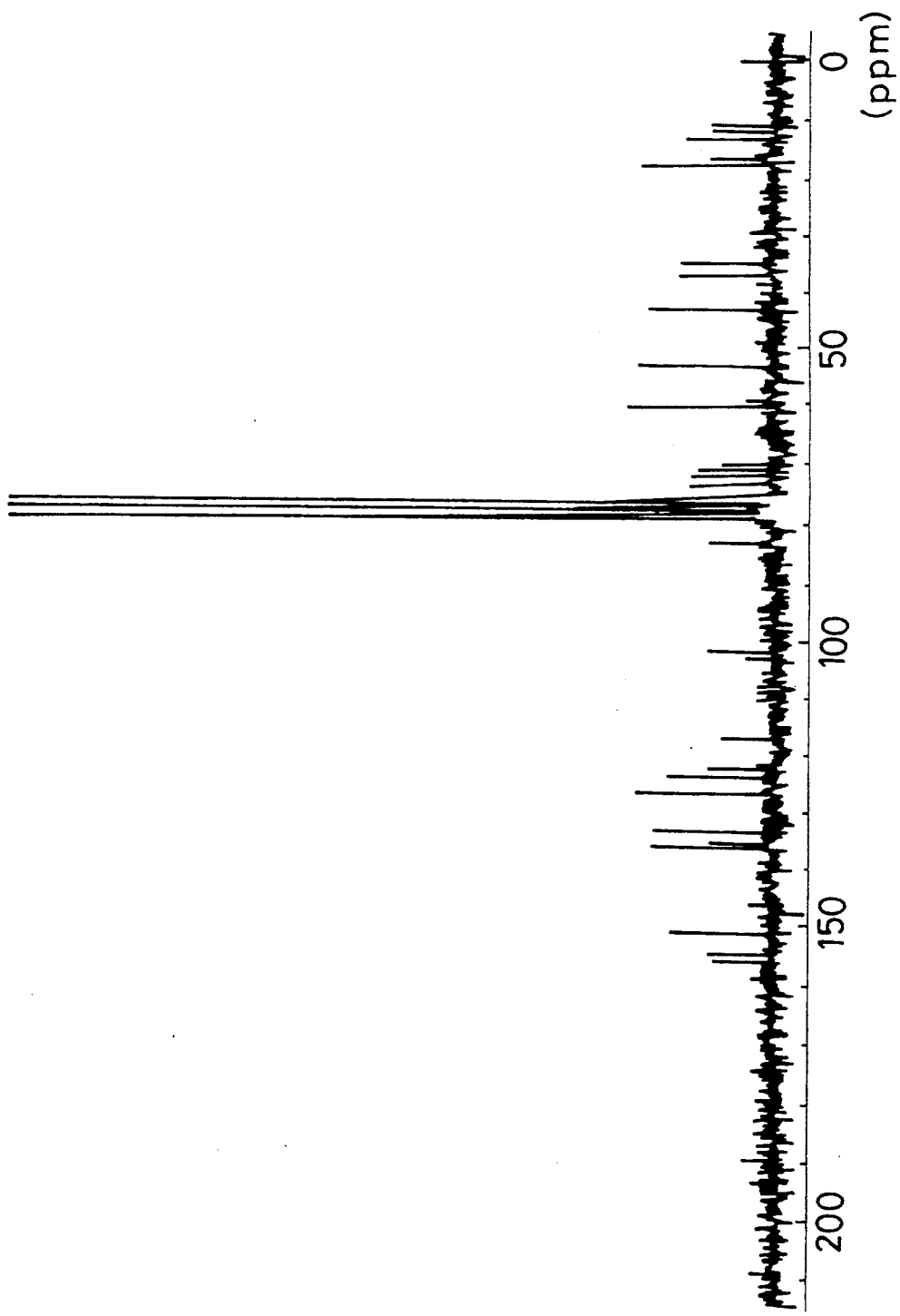
FIG. 4 shows $^{13}$C-NMR spectrum of the SN-198C material.

(8) $^{13}$C-NMR Spectrum (22.5 MHz): FIG. 4

Measurement was made in a deuterated chloroform solution on the basis of TMS.

(9) Solubility: Soluble in chloroform, dimethyl sulfoxide, methanol and acetone. Insoluble in n-hexane and water.

(10) Color and properties of the material: White powder

(11) Thin-layer chromatography: Carrier: Silica gel plate F254 (made by E. Merck AG)

| Developing Solvent | Rf Value |
|---|---|
| Chloroform/methanol (5:1) | 0.49 |

(12) Structural formula

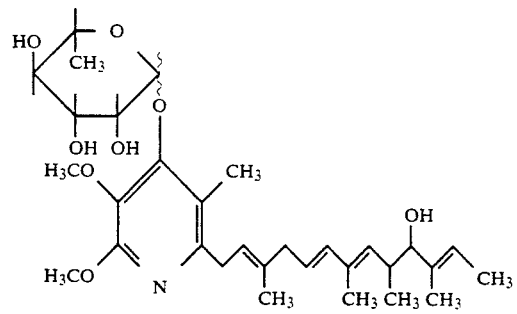

Furthermore, in the present invention, a series of compounds may be produced at times in which OH of the piericidin group is replaced with $CH_3$ or $OCH_3$. The present invention can recover these compounds by a suitable means.

Function

The physiologically active material SN-198C of the present invention has the following physiological activities:

(1) Antibacterial Activity

The antibacterial activisty of the physiologically active material SN-198C to various microorganisms can be indicated by a size of a growth inhibition circle to which the material is added in an amount of 20 $\mu$g/disc (diameter 8 mm). The results are set forth in Table 2. The value in paretheses in the table denotes a partial inhibition.

TABLE 2

| Microorganisms to be Inspected | Inhibition Circle (mm) |
|---|---|
| *Escherichia coli* AB 1157 | 0 |
| *Escherichia coli* BE 1186 | 0 |
| *Pseudomonas aeruginosa* IFO 13130 | 0 |
| *Pseudomonas aeruginosa* N-10 L-form | 14.0 |
| *Alternaria mali* IFO 8984 | 0 |
| *Colletotrichum lagenarium* IFO 7513 | (13.3) |
| *Pyricularia oryzae* IFO 5994 | 19.1 |
| *Candida albicans* IFO 1594 | 0 |
| *Chlorella vulgaris* | 0 |

(2) Cell-Killing Activity

A concentration of the physiologically active material SN-198C at which 50% of cancer cells are killed is set forth in Table 3.

TABLE 3

| Cells to be Inspected | $ID_{50}$ (μg/ml) |
|---|---|
| KB | 0.74 |
| HeLa | 2.8 |

EXAMPLE

A liquid medium containing 2% of glucose, 1% of soluble starch, 2.5% of soybean flour, 0.1% of meat extract, 0.4% of dried yeast, 0.2% of sodium chloride and 0.005% of potassium hydrogenphosphate was adjusted to a pH of 7.0, and 70 ml of the liquid medium was poured into a 500-milliliter flask and then sterilized. Afterward, streptomyces SN-198 strain (FERM BP-2884) was inoculated into the sterilized liquid medium and then cultivated at 27° C. for 2 days. In a 200-liter tank was placed 120 liters of the same kind of medium, and the latter was then sterilized. Into this medium, 2.4 liters of the above-mentioned seed culture medium was inoculated, and cultivation was done then under conditions of cultivation temperature 27° C., pH 8.3, stirring number 200 rpm and an aeration rate 120 liters/minute for 68 hours. In order to prevent foaming, a defoamer was suitably added thereto. Afterward, the thus obtained culture medium was separated by a centrifugal force into mycelia and a filtrate of the culture medium. Acetone was then added to the mycelia, followed by stirring and filtering, and the resulting filtrate was concentrated at 40° C. under reduced pressure. Next, water was added to the concentrated liquid and the latter was then extracted 3 times with ethyl acetate. On the other hand, the above-mentioned filtrate of the culture medium was also extracted 3 times with an equal amount of ethyl acetate, and the resulting extract was then joined to the aforesaid extract of the mycelia. The solvent was distilled off under reduced pressure at 40° C., so that 111.2 g of an oily crude extract was obtained.

Afterward, this crude extract was washed with n-hexane and then subjected to silica gel (Kisel gel 60, 70 to 230 mesh, made by E. Merck AG) column chromatography (diameter 7.5 cm and length 80 cm), and elution was then carried out with 5 liters of a chloroform/methanol (98:2) solution, so that piericidin $A_1$ was eluted. Furthermore, the elution was likewise made with 5 liters of the same (94:6) solution to elute 6.61 g of a 198C fraction. The eluate was then passed twice through a reversed phase HPLC [column YMC, D-ODS-5 and 20φ×250 mm; flow rate 10 ml/minute; detector UV (220 nm)]. The separated liquid was concentrated under reduced pressure and then freeze-dried, whereby 20 mg of a pure white 198C powder was finally obtained.

It was confirmed that the thus obtained product had the above-mentioned physical and chemical properties.

EFFECTS OF THE INVENTION

When the present invention is practiced, the SN-198C material which is a kind of novel piericidin compound can be obtained.

The SN-198C material has rhamnose of a molecular weight 164 at the $C_3'$ position thereof and is also different from already reported piericidins and glucopiericidin B in which D-glucose is bonded to the hydroxyl group at the $C_3'$ position [Journal of Antibiotics, 40, p. 149-156 (1987), and Japanese Laid-open Patent Publication No. 61-291594], and therefore new specificities of the SN-198C material can be expected.

In particular, the present material has antibacterial activity and cancer cells-killing effect, and so it can be expected as a medicine such as an antibiotic or agricultural chemicals.

What is claimed is:
1. A compound having the following structural formula

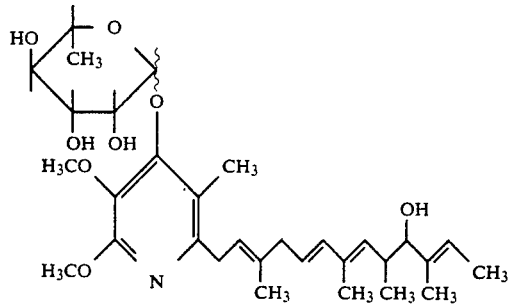

wherein R is OH, $CH_3$ or $OCH_3$.
2. The compound of claim 1, wherein R is OH.
3. The compound of claim 1, wherein R is $CH_3$.
4. The compound of claim 1, wherein R is $OCH_3$.

* * * * *